US005411948A

United States Patent [19]
Lingwood et al.

[11] Patent Number: 5,411,948
[45] Date of Patent: May 2, 1995

[54] USE OF HOST CELL PHOSPHOLIPIDS FOR INHIBITING MICROBIAL COLONIZATION

[75] Inventors: Clifford A. Lingwood, Toronto, Canada; Howard C. Krivan, Derwood, Md.; Bo Nilsson, Lund, Sweden

[73] Assignees: HCS Research and Development, Toronto, Canada; MicroCarb, Inc., Gaithersburg, Md.

[21] Appl. No.: 78,474

[22] Filed: Jun. 16, 1993

Related U.S. Application Data

[63] Continuation of Ser. No. 632,372, Dec. 21, 1990, abandoned.

[51] Int. Cl.⁶ ............................................. A61K 31/685
[52] U.S. Cl. ......................................... 514/78; 514/25; 514/54; 514/120; 514/121
[58] Field of Search .................... 260/403; 514/25, 54, 514/78, 77, 120, 121; 536/53; 435/261

[56] References Cited

U.S. PATENT DOCUMENTS 4,666,893  5/1987  Tsuchiya ................. 514/78
4,859,769  8/1989  Karlsson et al ......... 536/53

FOREIGN PATENT DOCUMENTS 0092121  4/1983  European Pat. Off. .

OTHER PUBLICATIONS

Citovsky et al.; Exp. Cell Res. 166: 279–94 (1986).
Krivan et al. PNAS 85:6157–61 (1988).
Krivan et al. Arch. Biochem. Biophys. 260(1):493–6 (1988).
Herrmann et al. Biochem. 29: 4054–8 (1990).
Mastromarino et al. Med. Micro. Immuno. 179(2) 105–14 (1990).
Willoughby et al. J. Vir. 64(10): 4830–5 (Oct. 1990).

*Primary Examiner*—Peter O'Sullivan
*Attorney, Agent, or Firm*—Pennie & Edmonds

[57] ABSTRACT

Methods for the in vitro and in vivo inhibition of microbial colonization are provided. The methods use host cell phospholipid molecules ("receptors") which bind microorganisms.

12 Claims, No Drawings

USE OF HOST CELL PHOSPHOLIPIDS FOR INHIBITING MICROBIAL COLONIZATION

CROSS-REFERENCE TO RELATED APPLICATION

This application is a continuation of U.S. patent application Ser. No. 07/632,372, filed Dec. 21, 1990 (now abandoned).

TECHNICAL FIELD

The present invention relates generally to methods of using phospholipid receptors which bind microorganisms.

BACKGROUND OF THE INVENTION

The process by which microorganisms bind to host cells is called adherence or adhesion, and it is now well accepted that this mechanism is an important step in the initiation of microbial colonization and infection. Generally, host cells possess structures ("receptors") that mediate binding of infectious microorganisms. Therefore, the receptors on host tissue are just as much a determinant of microbial infectivity as are the structures on microorganisms that mediate binding.

An example of a pathogenic microorganism of concern to humans is *Chlamydia trachomatis*. This microorganism is an obligate intracellular bacterial parasite of eucaryotic cells and is now known to be the most common sexually transmitted pathogen in industrialized societies (Moulder in *Microbiology of Chlamydia*, ed. A. L. Barron, pages 3–19, CRC Press, Boca Raton, Fla., 1988; Schachter in *Microbiology of Chlamydia*, pages 153–166, 1988). In the United States, it has been estimated that more than four million people contract chlamydial-related diseases each year (Eisner & Monahan, *Diagnostics and Clin. Testing* 28:26–28, 1990). Salpingitis, ectopic pregnancy, infertility, chronic pelvic pain, premature labor, neonatal conjunctivitis, infant pneumonia, endemic trachoma, urethritis, and epididymitis have all been directly or indirectly related to infection by the organism (Schachter 1988; Eisner & Monahan, 1990).

Another example of a pathogenic microorganism of concern to humans is *Helicobacter pylori*. This microorganism is an infectious agent of the human stomach. Infection is associated with both primary, chronic-active gastritis, and peptic ulcer disease (Blaser, *J. Infect. Dis.* 161:621-623, 1990; Marshall, *J. Infect. Dis.* 953:650-657, 1986; Marshall et al., *Lancet* ii:1437-1442, 1988). Each year there are more than 300,000 new cases, 3,200,000 recurrences, and 3,200 deaths from duodenal disease in North America (Schefler, *Statistics for Health Professionals*, 1984). One and one half percent of all worker absenteeism in North America is a result of peptic ulcers (Jansen, *Am. J. Med.* 81:42-48, 1986). Antral gastritis is associated in turn with gastrointestinal carcinoma (Johansenn and Sikjay, *Acta Path. Microbiol. Scan.* 85:240, 1977) and recent studies have linked *H. pylori* with GI cancer (Parsonnet et al., 30*th Interscience Conference on Antimicrobial Agents and Chemotherapy*, Atlanta, Ga., Oct. 21-24, 1990, abst. no. 5).

Due to the difficulties in current approaches to the prevention and treatment of microbial diseases, there is a need in the art for improved methods and compositions for preventing and treating microbial diseases. The present invention fills this need, and further provides other related advantages.

SUMMARY OF THE INVENTION

Briefly stated, the present invention provides a variety of in vitro and in vivo methods for the inhibition of microbial colonization. In one aspect of the present invention, methods for inhibiting microbial colonization in a biological preparation are provided. In one embodiment, the method comprises contacting a biological preparation with an effective amount of a phospholipid having the formula:

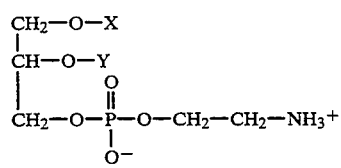

wherein X is

or $-CH_2=CH-R'$;

Y is

and

R' is an alkyl group and R are alkyl, hydroxyalkyl or alkenyl groups of fatty acids.

In another embodiment, the method comprises contacting a biological preparation with a phospholipid as described above in combination with GalNAc$\beta$1→4Gal$\beta$1→4Glc-Ceramide.

In another embodiment, the method comprises contacting a biological preparation with a phospholipid described above in combination with Gal$\beta$1→3GalNAc$\beta$1→4Gal$\beta$1→4Glc-Ceramide.

Another aspect of the present invention provides methods for removing a microorganism from a biological preparation. In one embodiment, the method comprises contacting a phospholipid with a biological preparation, suspected of containing a microorganism, under conditions and for a time sufficient to allow binding between said phospholipid and said microorganism, said phospholipid having the formula:

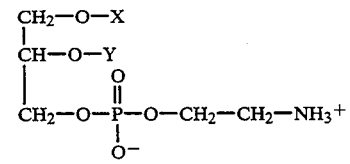

wherein X is

or $-CH=CH-R'$;

Y is

and

R' is an alkyl group and R are alkyl, hydroxyalkyl or alkenyl groups of fatty acids; and separating said phospholipid from said biological preparation, thereby removing the microorganism from the biological preparation.

In another embodiment, the phospholipid is in combination with GalNAcβ1→4Galβ1→4Glc-Ceramide and the step of separating comprises separating the phospholipid and the GalNAcβ1→4Galβ1→4Glc-Ceramide from the biological preparation.

In another embodiment, the phospholipid is in combination with Galβ1→3GalNAcβ1→4Galβ1→4Glc-Ceramide and the step of separating comprises separating the phospholipid and the Galβ1→3GalNAcβ1→4Galβ1→4Glc-Ceramide from the biological preparation.

For any of the embodiments, one or more of a phospholipid, GalNAcβ1→4Galβ1→4Glc-Ceramide or Galβ1→3GalNAcβ1→4Galβ1→4Glc-Ceramide may be immobilized on a solid support.

Within a related aspect, the present invention provides methods for inhibiting microbial colonization in a warm-blooded animal. In one embodiment, the method comprises administering to a warm-blooded animal an effective amount of a composition comprising a pharmaceutically acceptable carrier or diluent in combination with a phospholipid having the formula:

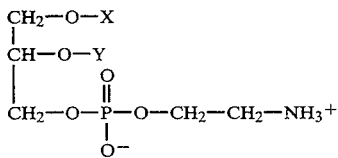

wherein X is

or —CH=CH—R';
Y is

and

R' is an alkyl group and R are alkyl, hydroxyalkyl or alkenyl groups of fatty acids.

In another embodiment, the method comprises administering to a warm-blooded animal an effective amount of the composition additionally including GalNAcβ1→4Galβ1→4Glc-Ceramide.

In another embodiment, the method comprises administering to a warm-blooded animal an effective amount of the composition additionally including Galβ1→3GalNAcβ1→4Galβ1→4Glc-Ceramide.

These and other aspects of the present invention will become evident upon reference to the following detailed description.

DETAILED DESCRIPTION OF THE INVENTION

As noted above, an important step in the initiation of microbial colonization and infection is the adherence of microorganisms to host cells. Microorganisms bind specifically to host cell receptors. Within the present invention, phospholipids are shown to be receptors for microorganisms and may be used to inhibit microbial colonization.

As disclosed within the present invention, a variety of microorganisms bind specifically to phospholipids isolated from human cells. Such microorganisms include Streptococci, Borrelia, Haemophilus, Pseudomonas, Neisseria, Helicobacter, Pasteurella, Campylobacter, Erysipelothrix, Gardnerella, Propionibacterium, Treponema, Clostridium, Shigella, Bacteriodes, Fusobacterium, Chlamydia, Mycobacterium, Yersina, Coxiella, Vibrio, Peptostreptococcus, Salmonella, and Mobiluncus. Typically, the host receptors for these microorganisms may be found on epithelial cells of the respiratory tract, gastrointestinal tract, or reproductive tract, or on blood or epidermal cells. Representative cultured cell lines include human oropharyngeal epithelial cells, human tracheal epithelial cells, human endometrial cells, human embryonic amnion cells, human gingival fibroblasts, HeLa cells, and McCoy cells.

Purification of the phospholipids responsible for binding (i.e., "receptor") may be accomplished by a combination of extractions and chromatographic procedures. For example, briefly, cells (such as HeLa) are washed with phosphate buffered saline and extracted using chloroform/methanol/water. The extract is centrifuged, the pellet re-extracted, and the supernates combined ("lipid extract"). The lipid extract is applied to an anion exchange resin and, after a methanol wash, the receptor fraction is eluted with methanol containing 10-20 mM NH₄HCO₃. Following evaporation of the solvent and re-dissolving in 1:1 methanol-chloroform, the receptor fraction is further purified by preparative thin-layer chromatography, e.g., silica gel. The band containing the receptor is transferred to a glass column, washed with chloroform, and eluted with methanol. Purity may be assessed by analytical thin-layer chromatography.

The disclosure of the present invention shows that a purified receptor comprises the following phospholipid structure containing ethanolamine and several different fatty acids:

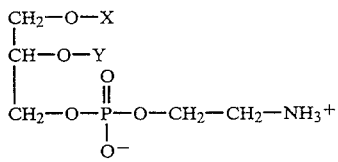

X is

or —C=CH—R' and
Y is

R represents alkyl, hydroxyalkyl and alkenyl chains of fatty acids, and R' is an alkyl chain.

Fatty acids are typically abbreviated by numerical designations. For example, $CH_3(CH_2)_{12}CH_2CH_2COOH$ is 16:0 where the number to the left of the colon indicates the number of carbon atoms and the number to the right indicates the number of double bonds. The fatty acids identified in the purified receptor phospholipids from HeLa cells are 16:0, 18:1, 18:0, 20:4, and 18:9OH+18:10OH, and are present in relative proportions of about 16%, 17%, 47%, 1%, and 19%, respectively. This collection of phospholipids binds microorganisms specifically and with high avidity. Phospholipids of this type, but missing one or more of these particular fatty acids, also bind microorganisms.

In addition to the phospholipids described above, microorganisms also bind strongly to specific glycolipids. In particular, the GalNAc$\beta$1→4Gal$\beta$1→4Glc sequences found in the glycolipids asialo-GM1 and asialo-GM2 appear to constitute a second receptor for microorganisms. Asialo-GM1 is the abbreviation for Gal$\beta$1→3GalNAc$\beta$1→4Gal$\beta$1→4Glc-Ceramide and asialo-GM2 has the same structure minus the terminal Gal. Ceramides are sphingolipid bases which are acylated on the amine with a fatty acid.

The phospholipids of the present invention may be administered as a composition, which includes a pharmaceutically acceptable carrier or diluent, to a warm-blooded animal (such as a human) for inhibiting microbial colonization. Alternatively, such compositions may include one or more of the glycolipids described above. The precise optimal dose may vary, depending upon the particular phospholipid or glycolipid used. Generally, however, an effective amount will be from about 0.1 to about 10 mg per kg body weight. These phospholipids and glycolipids provide a means for preventing colonization by, for example, "fooling" a microorganism into binding to them (i.e., as an artificial receptor), rather than to a native receptor on a host cell.

Pharmaceutically acceptable carriers and diluents include water, physiological saline, liposomes, alcohols, dimethyl sulfoxide (DMSO) and mixtures thereof. A composition may be administered by a variety of routes, including oral, parenteral and transdermal administration. For oral administration, the composition may be in pill, capsule or liquid form. For administration by injection, physiological saline is a preferred diluent. For transdermal administration, DMSO is a preferred carrier.

The receptor phospholipids of the present invention may also be used, individually or collectively, for in vitro inhibition of microbial colonization, such as in a biological preparation. The term "biological preparation" includes biological samples taken in vivo and in vitro (either with or without subsequent manipulation), as well as those prepared synthetically. Representative examples of biological preparations include cells, tissues, solutions and bodily fluids, such as (or from) blood, urine, saliva, sweat, synovial, cerebrospinal and tears. Briefly, one or more of the receptor phospholipids are added to a biological preparation. Alternatively, such phospholipids may include one or more of the glycolipids described above. The precise optimal concentration may vary, depending upon the particular phospholipid or glycolipid used. Generally, however, a concentration of about 1 to 100 mg per ml will be effective. As noted above, these phospholipids and glycolipids prevent binding of microorganisms to native receptors on host cells. Accordingly, one of the uses of this aspect of the present invention is to prevent microbial colonization of a biological preparation during its storage.

It may be desirable to add to a biological preparation a phospholipid (and/or glycolipid) which has been immobilized to a solid support. This variation permits removal of the phospholipid (and/or glycolipid), to which a microorganism may be bound, prior to use of the biological preparation. A phospholipid (and/or glycolipid) may be immobilized onto a solid support by adsorption or covalent attachment. It will be evident to those skilled in the art that the receptor may be covalently attached in a variety of ways, including photoactivation and linker groups such as the homo- and hetero-functional reagents available from Pierce Chemical Co. (Rockford, Ill.).

The following examples are offered by way of illustration and not by way of limitation.

EXAMPLES

EXAMPLE 1

BINDING OF CHLAMYDIAL ORGANISMS TO LIPIDS

A. Growth and Radiolabeling of a Chlamydial Organism

A cervical isolate of *C. trachomatis* serovar E was grown in HeLa 229 cells and chlamydial elementary bodies (EBs) were purified by a modified procedure of a renograffin gradient procedure (Caldwell et al., *Infect. Immun.* 31:1161–1176, 1981; Bavoil et al., *Infect. Immun.* 44:478–485, 1984). The purified EBs were washed twice with phosphate buffered saline (PBS) and the density of the EBs was adjusted to that of McFarland No. 3 tube with PBS.

Chlamydial organisms were radioiodinated as described for bacteria (Krivan et al., *Arch. Biochem. Biophys.* 260:493–496, 1988), with minor modifications. Briefly, 0.5 ml of the chlamydial suspension were reacted with 0.5 mCi of Na$^{125}$I at an ice bath in a tube (10×75 mm) coated with 0.1 mg of Iodogen (Pierce Chemical Co., Rockford, Ill.). After 4 to 5 min, the suspension was transferred to a centrifuge tube containing 5 ml of Tris-BSA buffer (0.05M Tris hydrochloride [pH 7.8] containing 0.15M NaCl and 1% bovine serum albumin). The tube was centrifuged at 30,000×g for 30 min at 4° C. and the supernatant fluid was removed. The pellet was resuspended in 6 ml of Tris-BSA buffer and the centrifugation was repeated. The supernatant fluid was removed and the pellet was resuspended in 5 ml of Tris-BSA buffer. The radioactivity of the suspension was adjusted to 2×10$^6$ cpm/ml for a chromatogram overlay assay and to 4×10$^6$ for a solid-phase binding assay with RPMI-BSA (RPMI 1640 medium [GIBCO Laboratories, Grand Island, N.Y.] containing 1% BSA).

B. Sonic Extraction of Chlamydial Organisms and Radiolabeling of the Fraction

The purified EBs were sonicated for 7 min in an ice bath using a microtip followed by centrifugation at 4° C. for 30 min at 30,000×g. The supernatant fluid was designated as sonic extract and its protein concentration was determined by BCA protein assay (Pierce Chemical Co., Rockford, Ill.) using bovine serum albumin as a standard.

The sonic extract was radiolabeled as described for protein (Magnani et al., Meth. Enzymol. 83:235-241, 1982) with minor modifications. Briefly, 10 μg protein in 30 μl PBS of the sonic extract was mixed with 100 μl of 0.3M sodium phosphate buffer in an Iodogen-coated tube as described above. One mCi of Na$^{125}$I was added to the tube and the sonic extract was iodinated for 2 min in an ice bath with frequent shaking. The reaction mixture was transferred to a PD-10 Sephadex G-25M column (Pharmacia LKB, Upssala, Sweden) which was pre-equilibrated with Tris-BSA. After the mixture passed through the column, 1 ml of Tris-BSA was added to the top of the column and this was followed by adding more Tris-BSA. The first 1 ml was discarded and the next 5 ml was collected. The radioactivity of the sonic extract was adjusted to $2\times10^6$ cpm/ml for a chromatogram overlay assay and to $4\times10^6$ cpm/ml for a solid-phase binding assay with RPMI-BSA.

C. Chromatogram Overlay Assay for Binding of Chlamydial Organisms to Lipids

The overlay assay was performed as described for bacteria (Krivan et al., Arch. Biochem. Biophys. 260:493-496, 1988). Briefly, lipids were chromatographed on aluminum-backed silica gel high-performance thin-layer plates (HPTLC; E. Merck AG, Darmstadt, Federal Republic of Germany), and developed with chloroform-methanol-0.25% aqueous KCl (5:4:1). The plate was coated with polyisobutylmethacrylate (0.1% in hexane), air-dried, soaked for 1 h in Tris-BSA buffer, and overlayed for 2 h at room temperature with $^{125}$I-labeled either chlamydial organisms or chlamydial subcellular fraction as described above. The plates were gently washed to remove unbound organisms, dried, and exposed for 40 h to XAR-5 X-ray film (Eastman Kodak Co., Rochester, N.Y.).

D. Solid-Phase Assay for Binding of Chlamydial Organisms to Lipids

The solid-phase binding assay was performed as described by Krivan et al., Arch. Biochem. Biophys. 260:493-496, 1988. Briefly, serial dilutions of purified lipids in methanol (25 μl) containing cholesterol and phosphatidylcholine (0.1 μg each) were added to polyvinylchloride microdilution wells (Falcon 3919; Becton Dickinson and Co., Paramus, N.J.) and dried by evaporation. The wells were blocked with Tris-BSA for 1 h, rinsed with RPMI-BSA twice, and incubated with 25 μl of $^{125}$I-labeled either chlamydial organisms or its subcellular fraction for 2 h at room temperature. After the wells were washed five times with PBS, the polyvinylchloride wells were cut with scissors and placed in counting tubes. Binding was quantified in a gamma counter.

EXAMPLE 2

PURIFICATION AND CHARACTERIZATION OF CHLAMYDIA RECEPTOR

A. Purification

HeLa 229 were grown in TC-175 cm$^2$ flasks and harvested either by mild trypsinization or scrapping. Cells were washed three times in 0.0067M phosphate buffered saline (PBS, pH 7.2). Total lipids of HeLa 229 cells were extracted by adding three volumes (to the wet weight of the cells) of deionized water, ten volumes of methanol and five volumes of chloroform. The mixture was ultrasonicated for 2 min and incubated overnight on a rocking bed at room temperature. The extract was centrifuged at 4° C. for 5 min at 2,000 rpm. Supernatant fluid was saved and the pellet was resuspended in the same volumes of deionized water, methanol and chloroform. The suspension was ultrasonicated for 30 min and supernatant fluid was collected by centrifugation. The first and second supernatant fluids were combined in a round bottom flask and dried on a rotary evaporator.

The dried total lipid extract of HeLa 229 cells was solubilized in 1:1 methanol-chloroform (0.5 ml per 1 gram wet weight of the cells). A portion of the total lipid was stored at −20° C. for later analysis. The rest was dried under nitrogen and dissolved in the original volume of chloroform-methanol-water (30:60:8). The total lipids of HeLa 229 cells were applied to a DEAE-Sepharose CL-6B column (Pharmacia AB, Uppsala, Sweden) and allowed to bind for 20 min. Neutral lipids were eluted first with five gel volumes of methanol, then the fraction containing Chlamydia receptor ("receptor") was eluted with five gel volumes of methanol containing 10-20 mM NH$_4$HCO$_3$. Fractions containing receptor migrated between CMH and CDH as analyzed by HPTLC and were weakly orcinol positive. The phospholipid fractions were verified to contain the Chlamydia receptor by the ability to bind radiolabeled elementary bodies as analyzed by the chromatogram overlay assay described in Example 1. Other acidic lipids were eluted with five gel volumes of methanol containing 0.5M NH$_4$HCO$_3$. Each lipid elution was dried on a rotary evaporator and redissolved in 1:1 methanol-chloroform.

The fraction containing receptor was further purified by chromatographing on Silica Gel G-2000 microns thin-layer preparative plates (Anal. Tech, Newark, N.J.), developed with 5:4:1 chloroform-methanol-aqueous 0.25% KCl. The plates were sprayed with primuline and examined by a longwave U.V. light. The band containing receptor stains positive with primuline and binds Chlamydia in the chromatogram overlay assay as described in Example 1. The receptor band was scrapped out, minced and packed in a glass column. The column was washed with five gel volumes of chloroform, then receptor was eluted with ten gel volumes of methanol. This elution was rotary evaporated and redissolved to ½ of the original volume with 1:1 methanol-chloroform. The purity of receptor was examined by thin-layer chromatography, and its ability to function as the Chlamydia receptor was verified by chromatogram overlay assay, both procedures as described in Example 1.

B. Analyses

1. Chemical

Amino acid analysis (according to the procedures of Spackman et al., Anal. Chem. 30:1190-1206, 1958) of receptor revealed an absence of amino acids, but the presence of ethanolamine (10%-15% by weight). The results of fatty acid analysis (according to the procedure of Gaver & Sweeley, J. Am. Oil Chem. 42:294-298, 1965) of "bPE" (L-α-phosphatidylethanolamine from bovine brain, P8673 lot No. 69F-8365-1, Sigma Chemical Co., St. Louis, Mo.), and receptor are summarized in Table 1.

TABLE 1
Fatty Acid Composition of bPE and Receptor

| Fatty acid | % of total bPE | fatty acid content Receptor |
|---|---|---|
| C16:0 | 10.3 | 16.1 |
| C18:1[a] | 7.0 | 10.4 |
| C18:1[a] | 3.6 | 6.5 |
| C18:0 | 49.5 | 47.2 |
| C20:1 | 2.8 | — |
| C20:4 | — | 1.0 |
| C18:9OH + C18:10OH | 26.8 | 18.8 |

[a]Two different C18:1 unsaturated fatty acids

2. Mass Spectrometry

Fast atom bombardment mass spectra (FAB-MS) in negative ion mode were recorded on a VG ZAB-SE magnetic sector instrument. Samples were dissolved in triethanolamine and loaded on the stainless-steel target, which was bombarded with xenon atoms with a kinetic energy of 8 keV and an accelerating voltage of 10 kv was used. Gas-liquid chromatography-mass spectrometry (GLC-MS) in electron ionization mode was carried out on a VG 12-250 quadrupole instrument fitted with a DB-1 capillary column (0.25 mm×30 m). Spectra were recorded at 70 eV with an ion source temperature of 200° C. For gas-liquid chromatography (GLC), a Hewlett-Packard 5890 instrument was used, equipped with a flame ionization detector. Separations were performed on a DB-1 capillary column (0.25 mm×30 m).

FAB-MS in negative ion mode of bPE and receptor showed a complicated pattern of [M-1]$^-$ ions in the range of 600-900 mass units. Both compounds showed a considerable heterogeneity in the lipid portion. The molecular weight range is what can be expected for phosphatidylethanolamines. Subtraction of the bPE spectrum from the receptor spectrum indicated that receptor has a different lipid moiety than bPE.

3. NMR Spectroscopy $^1$H- and $^{13}$C-spectra were recorded on a Bruker AM-500 instrument. Spectra were obtained in CD$_3$OD at 27° C. and chemical shifts were expressed relative to internal tetramethylsilane set to 0 ppm (for $^1$H-spectra) or setting the central signal of the methyl-resonance in CD$_3$OD to 48.9 ppm (for $^{13}$C-spectra). Two dimensional proton-proton Correlation Spectroscopy (COSY) and Distortionless Enhancement of Polarisation Transfer (DEPT) spectra were obtained according to Bruker Spectrospin standard software program.

The $^1$H-spectra of receptor showed characteristic signals for a lipid with CH$_3$ groups (0.85 ppm) and CH$_2$ signals from aliphatic chains (1.3 ppm). Substantial amounts of unsaturations in the fatty acid chains were evident from the bulk of signals around 5.4 ppm. A number of signals not deriving from fatty acids were seen in the area of 6-3 ppm. Two spin systems of equal intensities and with similar features both containing five signals were detected.

The first system with multiplet signal at 5.23 ppm was through cross-peaks in the COSY-spectrum connected to two AB-systems (CH$_2$-groups judged from their T$_1$-relaxation), one at 4.43 ppm and 4.17 ppm and the other at 3.95 ppm (signal stemming from two protons). These features bear a close resemblance to glycerol substituted by fatty acids in positions 1 and 2 and a phosphor diester in position 3. (Birdsal et al., *J. Chem. Soc. Perkin II*:1441–45, 1972; Huang & Andersson, *J. Biol. Chem* 264:18667–72, 1989). The other spin system showed a similar pattern, CH$_2$ at 5.17 ppm and a two-proton resonance at 3.98 ppm. The second AB-system showed a marked shift of the other AB-system to 3.0 and 3.95 ppm. This may indicate a change from an acylated to an alkylated CH$_2$-group.

The two remaining signals, a doublet at 5.97 ppm connected to a quartet at 4.35 ppm, indicates a double bond in a structural element of:

$$-O-CH=CH-CH_2$$

Finally, two multiplets at 4.03 ppm and at 3.15 ppm in the ratio of 4:1 compared to the two glycerol units can be explained by the two CH$_2$-groups in a phosphorylated ethanolamine:

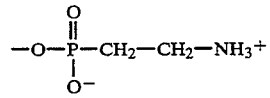

The above data suggest the following two structures in a 1:1 ratio:

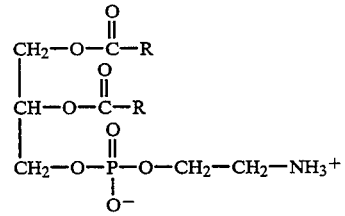

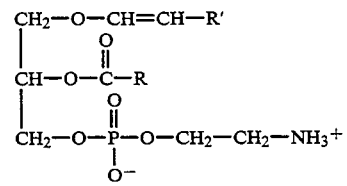

R and R' represent the hydrocarbon (or hydroxylated hydrocarbon) chains of fatty acids and plasmalogens, respectively. This interpretation was confirmed by recording a reference spectrum of L-α-phosphatidylethanolamine obtained from bovine brain (bPE) and stated to contain 54% plasmalogen (i.e., α, β unsaturated alkyl chains). The fit between the two spectra (receptor and bPE) was almost perfect, confirming the proposed structures. (The reference contained about 67% plasmalogen rather than 54% as stated.) $^{13}$C-spectra supported the above structures.

EXAMPLE 3

BINDING OF HELICOBACTER ORGANISMS TO LIPIDS

A. Growth of *H. pylori*

*H. pylori* isolates LC3 and LC11 were cultured from gastric mucosal biopsy samples from children with antral gastritis. The organisms were stored in brucella broth with 10% glycerol and 10% fetal bovine serum at −70° C. Cultures are typically stored for a maximum of 6 months. Cultures were plated on Skirrow's medium and incubated at 37° C. under reduced oxygen for 24 h. An inoculum from the plate was placed in 10 ml brucella broth supplemented with 10% fetal bovine calf serum in a disposable Erlenmeyer flask. The flask was placed with a loose screwtop in an evacuation jar and was incubated under reduced oxygen at 37° C. for 16 h with constant shaking at 70 rotations per minute. This method consistently resulted in growth of $10^4$ organisms per ml. The bacteria had a classic spiral, flagellate morphology when viewed under phase contrast microscopy. They were positive for urease, oxidase, and catalase.

B. Production of Antibodies to *H. pylori*

A whole cell *H. pylori* polyvalent antibody was produced by intravenous injection of a 1500 g New Zealand white rabbit with formalized *H. pylori* strain LC3. Bacteria ($10^4$) in 0.5 ml phosphate-buffered saline were injected, followed 2 and 6 weeks later by injections of $10^8$ organisms suspended in 1 ml phosphate-buffered saline. Antiserum was obtained by way of a venous catheter (with the rabbit under general anaesthesia) two weeks after the last injection. The presence of *H. pylori* antibody was shown by immunoblots of whole cell sonicates of six separate *H. pylori* isolates. The antibody reacted with the same proteins from each isolate.

C. Chromatogram Overlay Assay for Binding of *H. pylori* to Lipids

Lipid extracts (50 μg) were separated by thin-layer chromatography on plastic-backed sheets (Polygram SIL-G, Brinkman Instruments, Ontario, Canada) in chloroform/methanol/water, 65:25:4 (by volume). The plates were blocked in 3% gelatin at 37° C. for 2 h. After washing, the plates were incubated at room temperature in a carbon dioxide/hydrogen atmosphere with freshly cultured *H. pylori* in growth medium ($10^6$/ml). After 2 h incubation, the plates were washed in 100 mmol/l "tris" saline pH 7.6, incubated in a 1/600 dilution of rabbit *H. pylori* antiserum, and incubated for a further 2 h at room temperature. The plates were washed again and incubated with goat antibody to rabbit immunoglobulin conjugated with horseradish peroxidase (Bio-Rad, Richmond, Calif.) for 1 h at room temperature. After washing, bound organisms were visualized by addition to peroxidase substrate 4-chloro-1-naphthol (Sigma Chemical Co., St. Louis, Mo.) Incubations in the absence of *H. pylori* were carried out simultaneously.

EXAMPLE 4

PURIFICATION AND CHARACTERIZATION OF *H. PYLORI* RECEPTOR

A. Purification

Lipids were extracted from outdated red blood cells, mucosal scrapings of pig stomach and of human stomach obtained at necropsy, and cultured HEp2 cells. The tissue was weighed, homogenized in a minimum volume of water, and extracted in 20 volumes of chloroform/methanol 2:1 (by volume); the extract was then partitioned against water. The lower-phase lipids were dried, dissolved in chloroform/methanol 98:2, and applied to a silicic acid column previously equilibrated in chloroform. The column was washed extensively in sequence with chloroform, acetone/methanol 9:1 (3:1 for red blood cell extracts), and methanol. The fractions were dried and weighed. For further purification, the methanol fraction, which contained the Helicobacter-binding lipid, was concentrated, reapplied to a silicic acid column, and eluted with a linear gradient of chloroform/methanol 10:1 to 2:1. Fractions were concentrated and tested for binding by the thin-layer chromatography overlay assay as described in Example 3. Those containing the receptor were pooled.

B. Analyses

Phospholipids of human red blood cells and *H. pylori* receptor were separated by HPLC (as described by Heinz et al., *Chromatographia* 25:497–503, 1988). Fatty acids of the receptor phospholipids were analyzed by phospholipase digestion and HPLC (as described by Myher et al., *Lipids* 24:396–407, 1989). The results of fatty acid analysis of phosphatidylethanolamine from red blood cells (RBC PE") and receptor are summarized in Table 2.

TABLE 2

| Fatty Acid Composition of RBC PE and Receptor | | |
|---|---|---|
| | RECEPTOR AREA % | RBC PE AREA% |
| FAME + DMA FAME[1] | | |
| "16:0" | 15.05 | 12.18 |
| "17:0" | 0.32 | 0.21 |
| "18:0" | 8.71 | 6.11 |
| "18:1" | 19.69 | 15.79 |
| "18:2w6" | 4.44 | 5.37 |
| "20:1w9" | 0.61 | 0.30 |
| "20:2w6" | 0.40 | 0.21 |
| "20:3w6" | 1.01 | 0.85 |
| "20:4w6" | 17.67 | 20.34 |
| "20:5w3" | 0.10 | 0.60 |
| "22:4w6" | 5.15 | 5.58 |
| "22:5W3" | 0.59 | 0.87 |
| "22:5w3" | 2.12 | 3.19 |
| "22:6w3" | 3.33 | 4.64 |
| DMA[2] | | |
| "16:0" | 5.05 | 6.33 |
| "17:0" | 0.50 | 0.91 |
| "18:0" | 11.01 | 11.85 |
| "18:1" | 4.24 | 4.66 |

[1]Fatty acid methyl esters
[2]Dimethylacetals

From the foregoing, it will be evident that, although specific embodiments of the invention have been described herein for purposes of illustration, various modifications may be made without deviating from the spirit and scope of the invention.

We claim:

1. A method for specifically inhibiting bacterial colonization in a biological preparation, comprising:

contacting a biological preparation-suspected of containing bacteria selected from the group consisting of Streptococcus, Chlamydia, Clostridium, Staphylococcus, Borrelia, Haemophilus, Pseudomonas, Neisseria, Helicobacter, Shigella, Pasteurella, Coxiella, Mycobacterium, Salmonella, Fusobacterium, Bacteriodes, and Campylobacter, with an effective amount of phospholipid receptor having the formula:

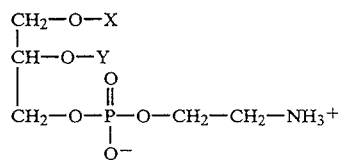

wherein X is

or —C═CH—R';
Y is

and

R' is an alkyl group and R is selected independently at each occurrence from alkyl, hydroxyalkyl or alkenyl groups of fatty acids for a time sufficient to allow said bacteria to specifically bind to and with said phospholipid receptor, thereby preventing binding of said bacteria to a native receptor on a host cell.

2. The method of claim 1 wherein the phospholipid is in combination with GalNAcβ1→4Galβ1→4Glc-Ceramide.

3. The method of claim 1 wherein the phospholipid is in combination with Galβ1→3GalNAcβ1→4Galβ1→4Glc-Ceramide.

4. A method for removing bacteria from a biological preparation, comprising:
contacting a biological preparation suspected of containing bacteria selected from the group consisting of Streptococcus, Chlamydia, Clostridium, Staphylococcus, Borrelia, Haemophilus, Pseudomonas, Neisseria, Helicobacter, Shigella, Pasteurella, Coxiella, Mycobacterium, Salmonella, Fusobacterium, Bacteriodes and Campylobacter, with a phospholipid receptor under conditions and for a time sufficient to allow specific binding between said phospholipid receptor and said bacteria said phospholipid receptor having the formula:

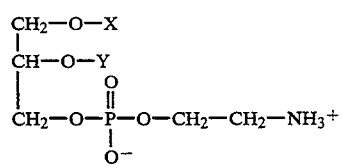

wherein X is 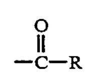 or —CH═CH—R';
Y is 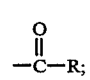 and
R' is an alkyl group and R is selected independently at each occurrence from alkyl, hydroxyalkyl or alkenyl groups of fatty acids; and
separating said phospholipid-bound bacteria from said biological preparation, thereby removing said bacteria from said biological preparation.

5. The method of claim 4 wherein the phospholipid is immobilized on a solid support.

6. The method of claim 4 wherein the phospholipid is in combination with GalNAcβ1→44Galβ1→4Glc-Ceramide and the step of separating comprises separating the phospholipid and the GalNAcβ1→4Galβ1→4Glc-Ceramide from the biological preparation, thereby removing the bacteria from the biological preparation.

7. The method of claim 6 wherein the phospholipid or the GalNAcβ1→4Galβ1→4Glc-Ceramide or both are immobilized on a solid support.

8. The method of claim 4 wherein the phospholipid is in combination with Galβ1→3GalNAcβ1→4Galβ1→4Glc-Ceramide and the step of separating comprises separating the phospholipid and the Galβ1→3GalNAcβ1→4Galβ1→4Glc-Ceramide from the biological preparation, thereby removing the bacteria from the biological preparation.

9. The method of claim 8 wherein the phospholipid or Galβ1→3GalNAcβ1→4Galβ1→4Glc-Ceramide or both are immobilized on a solid support.

10. A method for specifically inhibiting bacterial colonization in a warm-blooded animal, comprising:
administering to a warm-blooded animal suspected of being exposed to or infected by bacteria selected from the group consisting of Streptococcus, Chlamydia, Clostridium, Staphylococcus, Borrelia, Haemophilus, Pseudomonas, Neisseria, Helicobacter, Shigella, Pasteurella, Coxiella, Mycobacterium, Salmonella, Fusobacterium, Bacteriodes, and Campylobacter, an effective amount of a composition comprising a pharmaceutically acceptable carrier or diluent in combination with a phospholipid receptor having the formula::

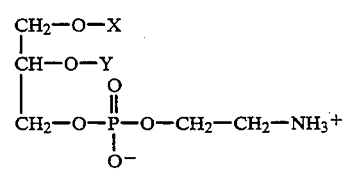

wherein X is 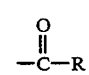 or —CH═CH—R';
Y is 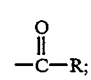 and
R' is an alkyl group and R is selected independently at each occurrence from alkyl, hydroxyalkyl or alkenyl groups of fatty acids, said phospholipid receptor having the ability to bind specifically to said bacteria, thereby preventing binding of said bacteria to a native receptor on host cell of said warm-blooded animal.

11. The method of claim 10 wherein the composition additionally includes GalNAcβ1→4Galβ1→4Glc-Ceramide.

12. The method of claim 10 wherein the composition additionally includes Galβ1→3GalNAcβ1→4Galβ1→4Glc-Ceramide.

* * * * *